(12) United States Patent
Puthiaparampil et al.

(10) Patent No.: US 7,301,046 B2
(45) Date of Patent: *Nov. 27, 2007

(54) BORONATE ESTERS

(75) Inventors: Tom Thomas Puthiaparampil, Bangalore (IN); Sumithra Srinath, Bangalore (IN); Madhavan Sridharan, Bangalore (IN); Sambasivam Ganesh, Bangalore (IN)

(73) Assignee: Biocon Limited, Electronics, Bangalore (IN)

( * ) Notice: Subject to any disclaimer, the term of this patent is extended or adjusted under 35 U.S.C. 154(b) by 302 days.

This patent is subject to a terminal disclaimer.

(21) Appl. No.: 10/505,528

(22) PCT Filed: Feb. 25, 2002

(86) PCT No.: PCT/IN02/00032

§ 371 (c)(1),
(2), (4) Date: Aug. 23, 2004

(87) PCT Pub. No.: WO03/070733

PCT Pub. Date: Aug. 28, 2003

(65) Prior Publication Data

US 2005/0154213 A1    Jul. 14, 2005

(51) Int. Cl.
*C07C 205/00* (2006.01)
*C07C 69/00* (2006.01)

(52) U.S. Cl. ...................... 560/125; 560/126

(58) Field of Classification Search ............... 560/125; 568/1

See application file for complete search history.

(56) References Cited

U.S. PATENT DOCUMENTS

| | | | |
|---|---|---|---|
| 5,399,722 A | 3/1995 | Beck et al. | |
| 5,481,009 A | 1/1996 | Matsumoto et al. | |
| 5,998,633 A | 12/1999 | Jacks et al. | |
| 6,140,527 A | 10/2000 | Kunihiro et al. | |
| 2005/0154213 A1 | 7/2005 | Puthiaparampil et al. | |
| 2006/0040898 A1* | 2/2006 | Puthiaparampil et al. | 514/64 |

FOREIGN PATENT DOCUMENTS

| | | |
|---|---|---|
| EP | 0 104 750 B1 | 4/1984 |
| EP | 0 319 847 B1 | 6/1989 |
| EP | 0 577 040 B1 | 1/1994 |
| EP | 0 909 757 A2 | 4/1999 |
| WO | WO-01/72706 A1 | 10/2001 |
| WO | 02057274 * | 7/2002 |
| WO | WO-02/057274 A1 | 7/2002 |
| WO | WO-03/070733 A1 | 8/2003 |

OTHER PUBLICATIONS

International Search Report, PCT/IN02/00032, Date of mailing Jun. 4, 2002.
Office Action Summary in U.S. Appl. No. 10/923,934, Date of mailing Jun. 25, 2006.

* cited by examiner

*Primary Examiner*—Karl Puttlitz
(74) *Attorney, Agent, or Firm*—Robin A. Weatherhead; Choate, Hall & Stewart LLP

(57) ABSTRACT

The present invention relates to optically active boronate derivatives which are useful as intermediates for the synthesis of HMG-CoA enzyme inhibitors such as atorvastatin, cerivastatin rosuvastatin, pitavastatin, and fluvastatin.

8 Claims, No Drawings

BORONATE ESTERS

PRIORITY CLAIM

The present application claims the benefit under 35 U.S.C. § 371 of International Application No. PCT/IN02/00032 (published PCT application No. WO 03/070733), filed 25 Feb. 2002, the entirety of which is hereby incorporated herein by reference.

FIELD OF THE INVENTION

The present invention relates to optically active boronate derivatives of formula IIa and more particularly to compounds of formula II which are useful as intermediates for the synthesis of HMG-COA enzyme inhibitors such as atorvastatin, cerivastatin, rosuvastatin, pitavastatin, and fluvastatin.

BACKGROUND OF THE INVENTION

Esters and derivatives of formula I:

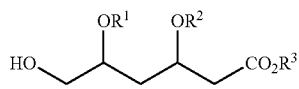

where $R^1$ and $R^2$ are independently chosen alkyl of one to three carbons and $R^3$ is alkyl of 1 to 8 carbon atoms, and alternatively compounds of formula Ia:

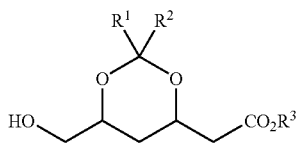

wherein $R^1$ and $R^2$ are independently chosen from alkyl of one to three carbons or phenyl, or $R^1$ and $R^2$ are taken together as —$(CH_2)_n$— wherein n is 4 or 5, and R is alkyl of 1 to 8 carbon atoms, are important intermediates in the preparation of compounds useful as anti-hypercholesterolemic agents having an inhibitory effect on HMG-COA reductase. Such agents include atorvastatin, cerivastatin, pitavastatin, fluvastatin and rosuvastatin.

Compounds of formula Ib:

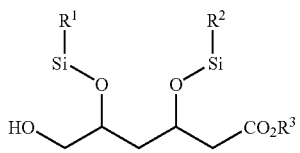

wherein $R^1$ and $R^2$ are alkyl of 1 to 5 carbons, and $R^3$ is as defined above, are also useful as intermediates in the preparation of said anti-hypercholesterolemic agents.

EP 0 319 847 describes a process for the preparation of compounds of formula I starting from L-malic acid. This process, however, suffers from the fact that the process is not industrially scalable and also possesses purification problems due to the non-crystalline nature of the intermediates.

U.S. Pat. No. 5,399,722 describes a process for preparing such compounds starting from commercially available ethyl ω-cloroacetoacetate or its benzyloxy derivative. The disadvantages of this process are that a stereo-selective reduction using a costly ruthenium-BINAP catalyst is employed and the desired compound of formula I is obtained in six steps.

U.S. Pat. No. 5,481,009 describes a five-step process for preparing such compounds starting from 4-phenyl-3-butenoic acid. The process uses both expensive materials such as N,O-dimethyl hydroxylamine and hazardous steps (ozonolysis) to obtain the desired product.

U.S. Pat. No. 5,998,633 describes a process for the preparation of protected esters of 3,4-dihydroxy butyric acid from a carbohydrate moiety which is transformed into the desired 3,4-dihydroxy butanoic acid derivatives in about 4 steps. The 3,4-dihydroxy butanoic acid derivative is then functionalized into compounds of formula I involving a multiple number of steps.

U.S. Pat. No. 6,140,527 describes a process for producing butyric acid derivatives starting from a butene derivative followed by reaction with a reagent capable of adding across the double bond. However, this procedure necessitates the need for a resolution step.

EP 0 104 750 describes a process for the preparation of 5-hydroxy-3-oxo pentanoic acid derivatives by alkylation of 3-hydroxybutyrate derivatives. The products of this process are racemic thus necessitating a resolution step.

The objective of the present invention is to provide a simple and industrially scalable process for the preparation of derivatives of formula I starting from commercially available and inexpensive materials.

SUMMARY OF THE INVENTION

To achieve said object, the present invention provides a compound of formula IIa:

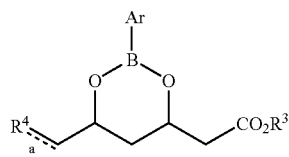

wherein:
Ar is unsubstituted or substituted aryl or heteroaryl;
$R^3$ is alkyl from 1 to 8 carbons, aryl or aralkyl;
$R^4$ is O, OH, CN or a halogen; and
a represents a single bond or double bond.

In certain embodiments, the present invention provides a compound of formula II:

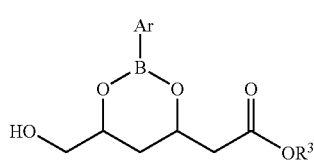

wherein:
 Ar is unsubstituted or substituted aryl or heteroaryl; and
 $R^3$ is alkyl from 1 to 8 carbons, aryl or aralkyl.

The present invention also provides a process for the manufacture of a compounds of formula II:

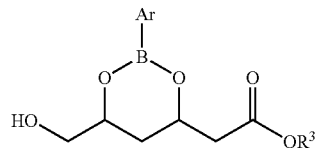

II wherein:
 Ar is unsubstituted or substituted aryl or heteroaryl; and
 $R^3$ is alkyl from 1 to 8 carbons, aryl or aralkyl, which comprises the steps of:
(a) reacting a compound of formula III:

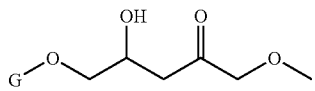

III where:
 G is tetrahydropyranyl, tert-butyldimethyl silyl, or trityl,
with the anion of tertiary butyl acetate to give a compound of formula IV:

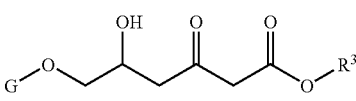

IV where:
 G is tetrahydropyranyl, tert-butyldimethyl silyl, or trityl; and
 $R^3$ is alkyl from 1 to 8 carbons, aryl or aralkyl,
(b) subjecting said compound of formula IV to reduction to give a compound of formula V:

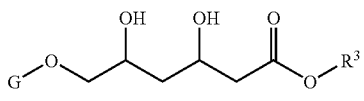

V where:
 G is tetrahydropyranyl, tert-butyldimethyl silyl, or trityl; and
 $R^3$ is alkyl from 1 to 8 carbons, aryl or aralkyl, (c) protecting the compound of formula V with $ArB(OH)_2$ to give a compound of formula VI:

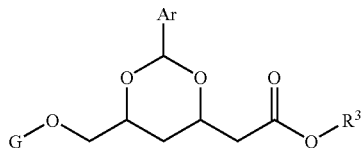

VI where:
 G is tetrahydropyranyl, tert-butyldimethyl silyl, or trityl; and
 $R^3$ is alkyl from 1 to 8 carbons, aryl or aralkyl, and
(d) deprotection of the compound of formula VI using mild acid catalyst to give a compound of formula II.

In certain embodiments, said $ArB(OH)_2$ is boronic acid.
In other embodiments, the compound of formula II:

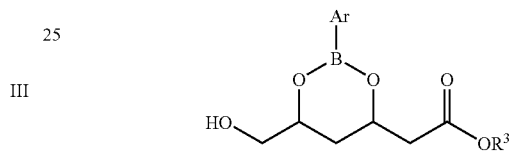

II wherein:
 Ar is unsubstituted or substituted aryl or heteroaryl; and
 $R^3$ is alkyl from 1 to 8 carbons, aryl or aralkyl, is oxidized to a compound of formula VIII:

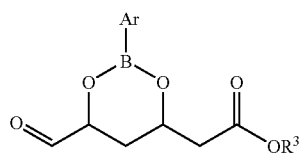

VIII wherein:
 Ar is unsubstituted or substituted aryl or heteroaryl; and
 $R^3$ is alkyl from 1 to 8 carbons, aryl or aralkyl, using pyridinium chlorochromate or DMSO/oxalyl chloride.
In yet other embodiments, the compound of formula II:

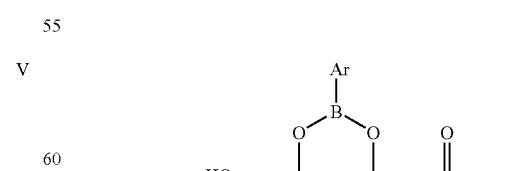

II wherein:
 Ar is unsubstituted or substituted aryl or heteroaryl; and
 $R^3$ is alkyl from 1 to 8 carbons, aryl or aralkyl, is further converted to a compound of formula IX:

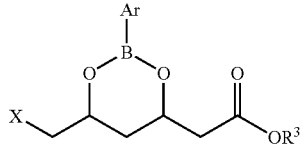

IX wherein:
Ar is unsubstituted or substituted aryl or heteroaryl;
R³ is alkyl from 1 to 8 carbons, aryl or aralkyl; and
X is a halogen.

In still other embodiments, the compound of formula IX:

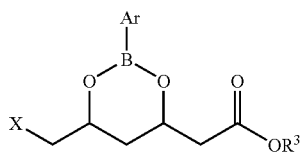

IX wherein:
Ar is unsubstituted or substituted aryl or heteroaryl;
R³ is alkyl from 1 to 8 carbons, aryl or aralkyl; and
X is a halogen, is further converted to a compound of formula VII:

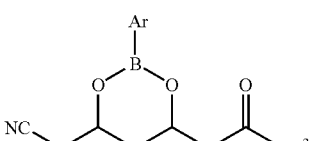

VII wherein:
Ar is unsubstituted or substituted aryl or heteroaryl; and
R³ is alkyl from 1 to 8 carbons, aryl or aralkyl.

In certain embodiments, a compound of formula IIa, and more particularly a compound of formula II, are used in the synthesis of atorvastatin, cerivastatin, pitavastatin, fluvastatin or rosuvastatin.

DETAILED DESCRIPTION OF THE INVENTION

Compounds of formula II serve as good intermediates for the synthesis of important substrates, which are useful in the synthesis of statins.

In certain embodiments, the hydroxyl moiety of formula II is converted into a facile leaving group by treating with tosyl chloride, methane sulfonyl chloride and the resulting intermediate can be displaced with cyanide to give compounds of formula VII:

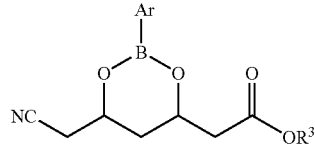

VII wherein Ar and R³ are as defined above.

In other embodiments, a compound of formula II can be is converted to a compound of formula IX

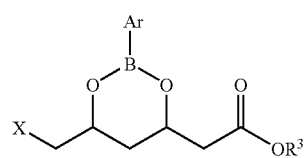

IX wherein Ar, R³ and X are as defined above, by reacting with aqueous HBr solution or by reaction with triphenyl phosphine and CBr₄ which is then converted to compound of formula VII.

According to another embodiment, the hydroxyl moiety of formula II is oxidized using standard procedures to give a compound of formula VIII:

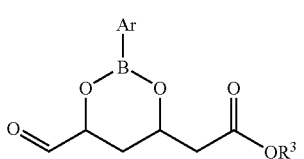

VIII wherein Ar and R³ are as defined above.

In still other embodiments, the present invention relates to optically active boronate derivatives of formula IIa which are useful intermediates for the synthesis of HMG-CoA enzyme inhibitors like atorvastatin, cerivastatin, rosuvastatin, pitavastatin, fluvastatin.

The invention is further illustrated with examples below, which are not intended to be limiting.

EXAMPLES

Example 1

Synthesis of methyl 4-triphenylmethyloxy-3-hydroxybutyrate: To 25 g of methyl 3,4-dihydroxybutanoate was added 250 mL of DCM and stirred to dissolve. 19.8 g of pyridine was added and cooled to 0° C. 41.4 g of trityl chloride was dissolved in 50 mL of DMC and was added at 0-5° C. for 15 minutes. The temperature was allowed to rise to room temperature and was stirred at room temperature for 17 hours. Water was added and the layers were separated. The organic layer was washed with brine, dried and concentrated. The residue was triturated with 25 mL of cyclohexane and the product was purified to give 15 g of the pure product.
$^1$H NMR (CDCl₃): 4.25 (m, 1H), 3.6 (s, 3H), 3.15 (d, 2H), 2.5 (m, 2H), 7.2-7.4 (m, 15H).

Example 2

Synthesis of tert-butyl 6-triphenylmethyloxy-5-hydroxy-3-oxohexanoate: 125 mL of THF and 24 g of diisopropylamine were charged and cooled to −15° C. 168 mL of 1.2 N n-BuLi was added at −15 to −5° C. and was stirred for 30 minutes. 21.56 g of tert-butyl acetate in 45 mL of THF, which was pre-cooled to −45° C., was added maintaining the temperature between −45 to −25° C. for 60 minutes. The reaction mixture was cooled to −45° C. and 30 g of methyl 4-triphenylmethyloxy-3-hydroxybutyrate in THF was added over a period of 20 minutes and the stirring was continued at −25° C. for 90 minutes. Water was added and the layers were separated. The aqueous layer was extracted using EtOAc and the combined organic layers were washed with brine, water, dried and concentrated to give the title compound which was used as such for the next step.

Example 3

Synthesis of tert-butyl 6-triphenylmethyloxy-3,5-dihydroxyhexanoate: To the crude tert-butyl 6-triphenylmethyloxy-5-hydroxy-3-oxohexanoate was added 150 mL of THF followed by 15 mL of MeOH and was chilled to −60° C. 26 mL of MDEB (50% solution in THF) was added over a period of 20 minutes and stirring was continued for a further 30 minutes. The reaction mixture was cooled to −80° C. and 5 g of sodium borohydride was added in portions and the after completion of addition the reaction mixture was stirred for 5 hours at −78° C. Acetic acid was added to adjust the pH to 7 and water was added. The aqueous layer was extracted using EtOAC, washed with brine, dried and concentrated to give the title compound which was used as such for the next step.

Example 4

Synthesis of tert-butyl-6-triphenylmethyloxy-3,5-phenylboranatohexanoate: The crude tert-butyl 6-triphenylmethyloxy-3,5-dihydroxyhexanoate was dissolved in 100 mL of toluene and 5.6 g of phenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 10 g of the title product.

Example 5

Synthesis of tert-butyl-6-hydroxy-3,5-phenylboranatohexanoate: To 5 g of tert-butyl-6-triphenylmethyloxy-3,5-phenylboranatohexanoate was added 20 mL of DCM and was chilled to 0° C. 5 mL of TFA was added and was stirred at 20° C. for 6 hours. Water was separated and the organic layer was washed with bicarbonate, brine, dried and concentrated to give the title product, which was purified by column chromatography. $^1$H NMR (CDCl$_3$): 7.7-7.8 (m, 2H), 7.4-7.5 (m, 1H), 7.3-7.4 (m, 2H), 4.5 (m, 1H), 4.2 (m, 1H), 3.6 (m, 1H), 3.5 (m, 1H), 2.55 (m, 1H), 2.45 (m, 1H), 2.0 (m, 1H), 1.7 (m, 1H) 1.5 (s, 9H).

Example 6

Synthesis of tert-butyl-6-cyano-3,5-phenylboranatohexanoate: 5 g of tert-butyl-6-hydroxy-3,5-phenylboranatohexanoate was taken in dichloromethane (50 mL) and pyridine (10 mL) was added. The contents were cooled to −10° C. and methanesulfonyl chloride (1 equivalent) was added drop wise. After 5-6 hours of stirring at 0° C., the contents were washed with bicarbonate, water and brine. The solvent was removed under reduced pressure to afford the O-methanesulfonyl derivative, which was used as such for the next step. The crude mesylate was taken in DMSO (5 volumes) and 1.5 equivalents of potassium cyanide was added. The contents were maintained at reflux for a period of 18-22 hours. DMSO was removed under reduced pressure and the contents were extracted using ethyl acetate and was washed with bisulfite, brine and solvent was removed under reduced pressure to afford the desired product.

Example 7

Synthesis of tert-butyl-6-oxo-3,5-phenylboranatohexanoate: 4.3 g of dimethylsulfoxide was added drop wise to a solution of 2.4 mL of oxalyl chloride in 100 mL of dichloromethane and the mixture maintained at −78° C. The mixture was stirred at that temperature for a period of 15 minutes and a solution of 5 g of tert-butyl-6-hydroxy-3,5-phenylboranatohexanoate dissolved in dichloromethane was added drop wise. After stirring for 15 minutes, 17 mL of triethyl amine was added and the reaction mixture was allowed to warm to ambient temperature over a 2 hour period. The reaction mixture was concentrated and the residue was dissolved in water and extracted using diethyl ether. Removal of solvent afforded the title compound.

Example 8

Synthesis of tert-butyl-6-triphenylmethyloxy-3,5(1-napththalenyl)boranatohexanoate: The crude tert-butyl 6-triphenylmethyloxy-3,5-dihydroxyhexanoate was dissolved in 100 mL of toluene and 7.1 g of 1-naphthalene boronic acid was added. Water was removed by azeotropic distillation over a period of 3 hours. The reaction mixture was cooled to room temperature and toluene was removed under reduced pressure. 30 mL of methanol was added and the precipitated solid was filtered to give 14 g of the title product.

Example 9

Synthesis of tert-butyl 6-triphenylmethyloxy-3,5-(2-methylphenyl)boranatohexanoate: The crude tert-butyl 6-triphenylmethyloxy-3,5-dihydroxyheanoate was dissolved in 100 mL of toluene and 6.1 g of 2-methylphenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product.

Example 10

Synthesis of tert-butyl 6-triphenylmethyloxy-3,5-(4-methoxyphenyl)boranatohexanoate: The crude tert-butyl 6-triphenylmethyloxy-3,5-dihydroxyhexanoate was dissolved in 100 mL of toluene and 6.3 g of 4-methoxyphenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product.

Example 11

Synthesis of tert-butyl 6-triphenylmethyloxy-3,5-(8-quinolinyl)boranatohexanoate: The crude tert-butyl 6-triphenylmethyloxy-3,5-dihydroxyhexanoate was dissolved in 100 mL of toluene and 6.1 g of quinoline-8-boronic acid was added. Water was removed by azeotropic distillation over a period of 3 hours. The reaction mixture was cooled to room temperature and toluene was removed under reduced pressure. 30 mL of methanol was added and the precipitated solid was filtered to give 11 g of the title product.

Example 12

Synthesis of tert-butyl-6-triphenylmethyloxy-3,5-(3-nitrophenyl)boranatohexanoate: The crude tert-butyl 6-triphenylmethyloxy-3,5-dihydroxyhexanoate was dissolved in 100 mL of toluene and 6.1 g of 3-nitrophenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 10 g of the title product.

Example 13

Synthesis of tert-butyl-6-triphenylmethyloxy-3,5-(2,6-difluorophenyl)boranatohexanoate: The crude tert-butyl 6-triphenylmethyloxy-3,5-dihydroxyhexanoate was dissolved in 100 mL of toluene and 6.3 g of 2,6-difluorophenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product.

We claim:

1. A compound of formulae:

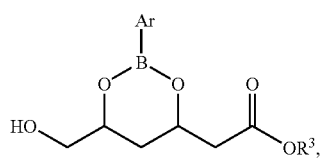
(II)

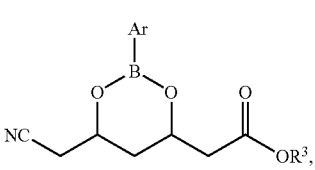
(VII)

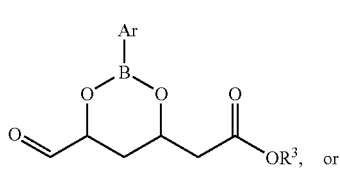
(VIII)

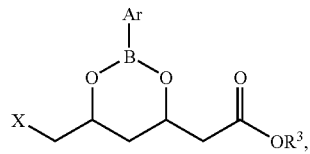
(IX)

wherein:
Ar is unsubstituted or substituted aryl or heteroaryl;
$R^3$ is alkyl from 1 to 8 carbons, aryl or aralkyl; and
X is a halogen.

2. The compound as claimed in claim 1 wherein said compound is a compound of formula II:

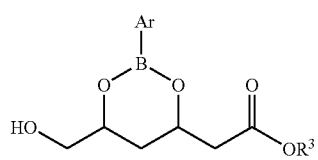
II wherein:
Ar is unsubstituted or substituted aryl or heteroaryl; and
$R^3$ is alkyl from 1 to 8 carbons, aryl or aralkyl.

3. A process for the manufacture of a compound of formula II

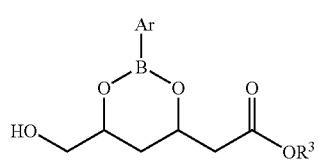
II wherein:
Ar is unsubstituted or substituted aryl or heteroaryl; and
$R^3$ is alkyl from 1 to 8 carbons, aryl or aralkyl,
which comprises the steps of:
(a) reacting a compound of formula III:

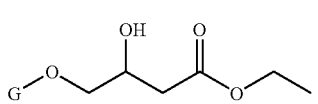
III where:
G is tetrahydropyranyl, tert-butyldimethyl silyl, or trityl,
with the anion of tertiary butyl acetate to give a compound of formula IV:

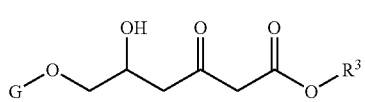
IV where:
G is tetrahydropyranyl, tert-butyldimethyl silyl or trityl; and
R³ is alkyl from 1 to 8 carbons, aryl or aralkyl,
(b) subjecting the compound of formula IV to reduction to give a compound of formula V:

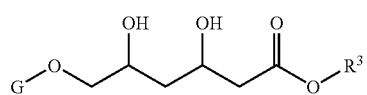

where:
G is tetrahydropyranyl, tert-butyldimethyl silyl or trityl; and
R³ is alkyl from 1 to 8 carbons, aryl or aralkyl,
(c) protecting the compound of formula V with ArB(OH)₂ to give a compound of formula VI:

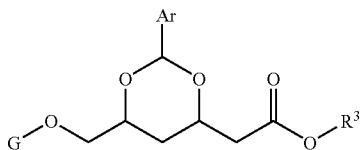

where:
Ar is unsubstituted or substituted aryl or heteroaryl;
G is tetrahydropyranyl, tert-butyldimethyl silyl or trityl; and
R³ is alkyl from 1 to 8 carbons, aryl or aralkyl, and
(d) deprotection of the compound of formula VI using mild acid catalyst to give a compound of formula II.

4. The process as claimed in claim 3 wherein ArB(OH)₂ is boronic acid.

5. The process as claimed in claim 3 wherein the compound of formula II:

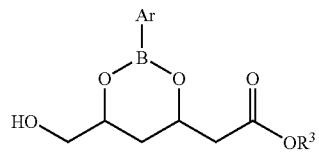

where:
Ar is unsubstituted or substituted aryl or heteroaryl; and
R³ is alkyl from 1 to 8 carbons, aryl or aralkyl,
is oxidized to a compound of formula VIII:

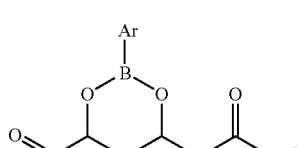

where:
R³ is alkyl from 1 to 8 carbons, aryl or aralkyl, and
Ar is unsubstituted or substituted aryl or heteroaryl, using pyridinium chloro chromate or DMSO/oxalyl chloride.

6. The process as claimed in claim 3 wherein the compound of formula II:

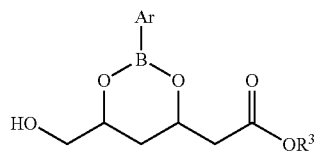

where:
Ar is unsubstituted or substituted aryl or heteroaryl; and
R³ is alkyl from 1 to 8 carbons, aryl or aralkyl,
is further converted to a compound of formula IX:

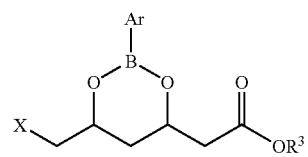

where:
R³ is alkyl from 1 to 8 carbons, aryl or aralkyl;
Ar is unsubstituted or substituted aryl or heteroaryl; and
X is a halogen.

7. The process as claimed in claim 6 wherein the compound of formula II is converted to compound of formula IX by reacting compound of formula II with aqueous HBr solution or by reaction with triphenyl phosphine and CBr₄.

8. The process as claimed in claim 6 or 7 wherein the compound of formula IX:

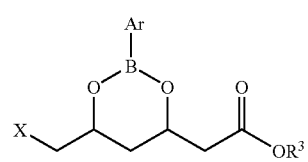

where:
R³ is alkyl from 1 to 8 carbons, aryl or aralkyl;
Ar is unsubstituted or substituted aryl or heteroaryl; and
X is a halogen,
is further converted to a compound of formula VII:

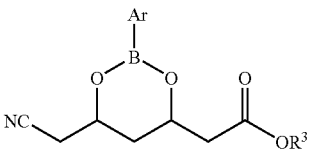

where:
R³ is alkyl from 1 to 8 carbons, aryl or aralkyl; and
Ar is unsubstituted or substituted aryl or heteroaryl.

* * * * *